United States Patent [19]
Mason

[11] Patent Number: 5,620,686
[45] Date of Patent: Apr. 15, 1997

[54] ANTIGEN-ANTIBODY CONJUGATES

[75] Inventor: Donald W. Mason, Witney, England

[73] Assignee: British Technology Group Limited, London, England

[21] Appl. No.: 454,747

[22] Filed: May 31, 1995

Related U.S. Application Data

[63] Continuation of Ser. No. 304,223, Sep. 12, 1994, abandoned, and a continuation-in-part of Ser. No. 39,481, filed as PCT/GB91/01641, Sep. 24, 1991 published as WO92/06120, Apr. 16, 1992, abandoned.

[30] Foreign Application Priority Data

Sep. 28, 1990 [GB] United Kingdom .................. 9021210
May 14, 1991 [GB] United Kingdom .................. 9110444

[51] Int. Cl.$^6$ ........................ C07K 16/46; A01K 39/395; C12N 15/85
[52] U.S. Cl. ..................... 424/134.1; 424/153.1; 424/173.1; 424/178.1; 530/391.7; 530/388.73; 530/389.6; 435/70.21; 435/172.2
[58] Field of Search ............................ 424/133.1, 134.1, 424/139.1, 152.1, 154.1, 173.1, 175.1, 178.1, 180.1, 153.1, 182.1; 435/69.6, 70.21, 172.1, 172.2, 240.27, 252.3, 252.33; 530/387.3, 388.22, 288.75, 389.6, 388.73, 391.7

[56] References Cited

U.S. PATENT DOCUMENTS 4,792,447 12/1988 Uhr et al. .............................. 424/85.91
5,045,451 9/1991 Uhr et al. ................................ 435/7.23

FOREIGN PATENT DOCUMENTS 8810120 12/1988 WIPO.
9010449 9/1990 WIPO.
9109619 7/1991 WIPO.

OTHER PUBLICATIONS

T.R. Mosmann et al., "TH1 and TH2 Cells: Different patterns of lymphokine secretion lead to different functional properties," Ann. Rev. Immunol 1, 145–73 (1989).

M.D. Sadick et al., "Cure of murine leishmaniasis with anti–interleukin 4 monoclonal antibody", J. Exp. Med. 171, 115–127 (1990).

F.D. Finkelman et al., "Production of BSF–1 during an in vivo T–dependent immune response", J. Immunol. 137, 2878–2885 (1986).

K.A. Krolick et al., "Selective killing of normal or neoplastic B cells by antibodies coupled to the A chain of ricin", Proc. Natl. Acad. Sci. USA 77, 5419–5423 (1980).

A. Lees et al., "Induction of large, rapid, specific antibody responses with antigen–anti–IGD antibody conjugates". FASEB Journal, 4, (7), A1804 (1990) (Joint Meeting Am. Soc. Biochem. and Mol. Biol. & Am. Assoc. Immunol. New Orleans USA, Jun. 4–7, 1990).

D.P. Snider et al., "Enhanced antigen immunogenicity induced by bispecific antibodies", J. Exp.Med. 171, 1957–1963 (1990).

S. Mjaaland et al., "Modulation of immune responses with monoclonal antibodies I. Effects on regional lymph node morphology and on anti–hapten responses to haptenized monoclonal antibodies" Eur. J. Immunol 20, 1457–1461 (1990).

R.E. Randall et al., "Humoral and cytotoxic T Cell Immune responses to internal and external structural proteins of Simian Virus 5 induced by immunization with solid matrix–antibody–anitgen complexes", J. Gen. Virol. 69, 2505–2516 (1988).

(List continued on next page.)

Primary Examiner—Christine M. Nucker
Assistant Examiner—Julie E. Reeves
Attorney, Agent, or Firm—Nixon & Vanderhye

[57] ABSTRACT

Diseases attribute to a predominantly cell-mediated immune response, notably autoimmune diseases, can be suppressed by administering a novel conjugate of an appropriate antigen, notably an autoantigen, with antibody to an appropriate B cell surface molecule, such as IgD.

4 Claims, 2 Drawing Sheets

OTHER PUBLICATIONS

C. Snapper et al., "Murine B cells expressing Thy-1 after in vivo immunization selectively secrete IgE", J. Immunol. 144 (8), 2940–2945 (Apr. 1990).

K. Ota et al., "T-cell recognition of an immunodominant myelin basic protein epitope in multiple sclerosis", Nature 346, 183–187 (12 Jul. 1990).

Abramowicz et al., The New England Journal of Medicine, p. 736, (Sep. 3, 1992).

Waldmann, Science, vol. 252, pp. 1657–1662 (1991).

Harris et al., TIBTECH. vol. 11, pp. 42–44 (1993).

Hawkins et al., BMJ, vol. 305, pp. 1348–1352 (Nov. 28, 1992).

Borrebaeck, Journal of Immunological Methods vol. 123, pp. 157–165 (1989).

Wells et al., Basic & Clinical Immunology, Fudenberg et al. (Eds), LANGE Medical Publications, Calif., pp. 390–409 (1976).

Byers et al., Basic & Clinical Immunology, Fudenberg et al, (Eds), LANGE Medical Publications, Calif., pp. 242–259 (1976).

ANTIGEN-ANTIBODY CONJUGATES

This is a Rule 62 continuation of application Ser. No. 08/304,223, filed 12 September 1994, now abandoned, and a Rule 62 continuation of application Ser. No. 08/039,481, filed as PCT/GB91/01641, Sep. 24, 1991 published as WO92/06120, Apr. 16, 1992, now abandoned.

BACKGROUND OF THE INVENTION

1. Field of the Invention

This invention relates to antigen-antibody conjugates and their therapeutic use.

2. Description of the Related Art

An autoimmune reaction is one mounted by the body against its own antigens. Certain specific diseases, notably rheumatoid arthritis and systemic lupus erythematosus, are ascribed to "autoantigens". It is widely believed that a specific class of active T cell lymphocytes is produced which recognises autoantigens.

There is evidence that T lymphocytes play an essential role not only in the induction of the immune response but also in its regulation. Specifically the lymphokines produced by certain populations of T cells can antagonize the effects of other activated T cells and thus modify their action. It is possible, and indeed likely, that defects in this immunoregulatory mechanism give rise to at least some autoimmune diseases.

The lymphokines IL-4 (previously called B cell stimulatory factor) and IL-10 (previously called cytokine synthesis inhibitory factor) are produced by certain T cells, specifically those which, after activation, promote humoral immunity, and these lymphokines have an inhibitory effect on cell-mediated immune responses, T. R. Mosmann and R. L. Coffman, Ann. Rev. Immuonl. 7, 145 (1989) and M. D. Sadick et al., J. Exp. Med. 171, 115 (January 1990). Consequently, those autoimmune diseases in which the pathogenesis is cell-mediated (rheumatoid arthritis is a likely example) might be effectively controlled if a strategy can be devised for inducing regulatory T cells that produce IL-4 (and IL-10) in response to the autoantigen.

Several years ago, it was shown that mice immunized with polyclonal antibodies to IgD produce high levels of IL-4 (IL-10 was not assayed), F. D. Finkelman et al., J. Immunol. 137, 2878 (1986).

SUMMARY OF THE INVENTION

It has now been shown that if an autoantigen which gives rise to a cell-mediated immune response is conjugated to an antibody to IgD, the cell-mediated process can be interrupted, with the result that the disease can be remarkably alleviated. It appears that the autoantigen supplied as an antibody-autoantigen conjugate causes the autoantigen to be presented to T cells by B cells (because the anti-IgD binds to the IgD on the B cells surface). This mode of presentation induces the T cells to produce IL-4 and IL-10 on subsequent encounter with the body's endogenous autoantigen. These lymphokines then suppress the action of potentially harmful T cells that are otherwise responsible for the tissue damage associated with autoimmunity. The same effect can be expected from non-auto antigens giving a cell-mediated immune response. As the lymphokines IL-4 and IL-10 have no intrinsic antigen specificity, the suppression that they mediate can, in principle, suppress T cells that are involved in cell-mediated responses to any antigen. However, for anatomical reasons such side effects will be unlikely.

According to the invention, therefore, there is provided a conjugate of (1) an antigen which gives rise to a harmful cell mediated immune response, especially an autoantigen, and (2) an antibody to surface molecules present predominantly on B cells, preferably to IgD.

The term "antigen" includes the natural antigen associated with particular symptoms, e.g. of a disease and fragments thereof, e.g. peptides, which have been found to stimulate the same symptoms.

The term "antibody" includes any ligand having the binding effect of a full length antibody, thus including Fab fragments, monoclonal antibodies, single domain antibodies and chimeric antibodies produced by recombinant DNA means, whereby the T cells are induced to release lymphokines.

The "conjugate" of (1) and (2) includes products comprising (1) bound to (2) by an effective means including ligand/anti-ligand or covalent bonding or both.

The term "surface molecule" includes any material presented on the cell surface, whether an immunoglobulin, e.g. IgD, or a ligand more commonly thought of as antigenic, e.g. a Class II MHC antigen. It must, however, be found mainly on B cells.

BRIEF DESCRIPTION OF THE ACCOMPANYING DRAWINGS

FIG. 1 is a simplified diagrammatic representation of effects considered to occur in the immune system; and FIG. 2 is a graph showing the effect of conjugates of the invention in suppressing an autoimmune disease.

DESCRIPTION OF THE PREFERRED EMBODIMENTS

Figure 1:
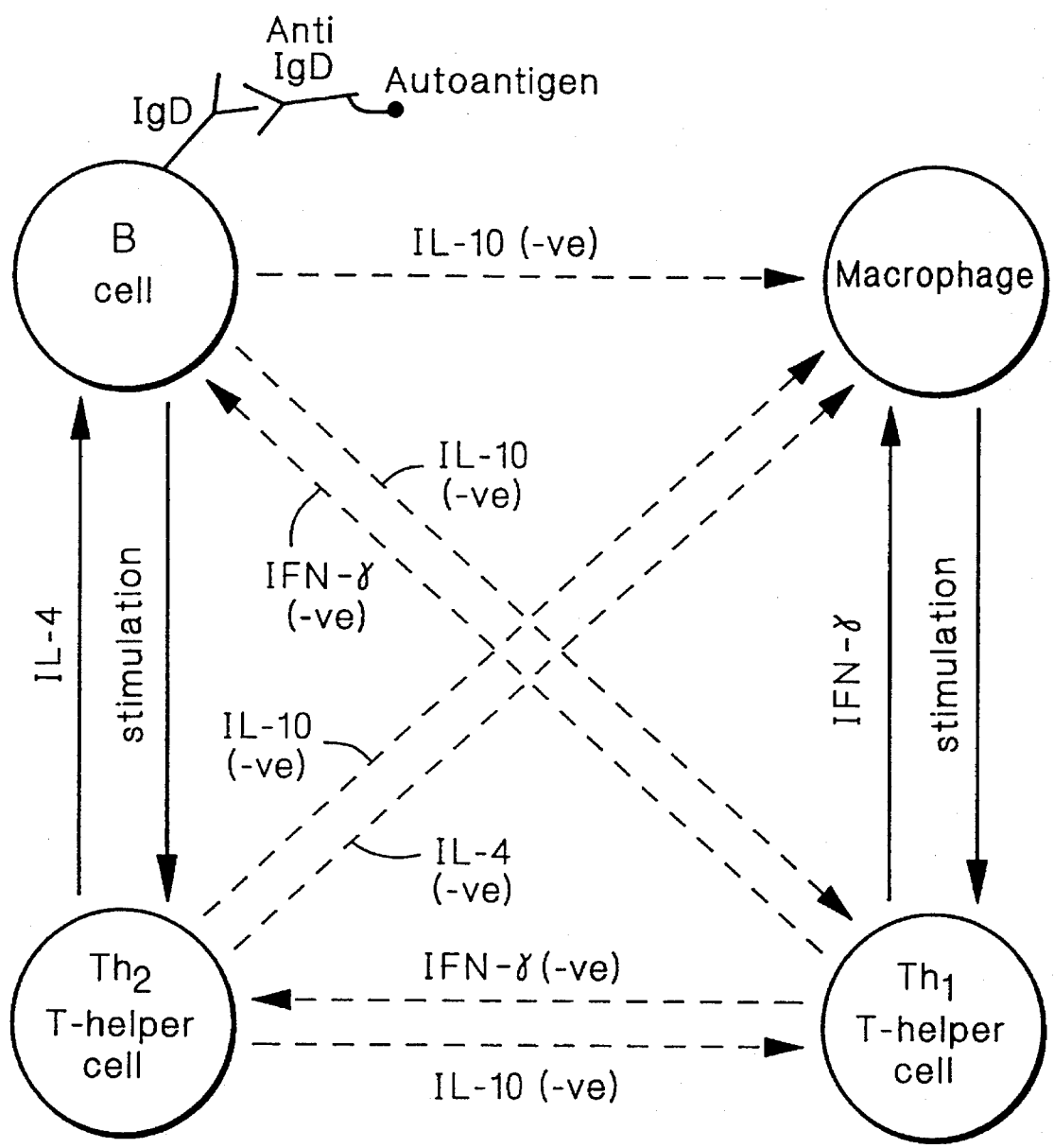

The invention is of interest principally for suppressing an autoimmune disease, e.g. rheumatoid arthritis. The antigen to be conjugated will therefore normally be an autoantigen. The invention is illustrated experimentally in the Example below by the conjugation of a peptide derived from guinea-pig myelin basic protein, amino acid residues 70–86. This peptide is known to stimulate experimental allergic encephalomyelitis (EAE), a "model" autoimmune disease, as described by I. A. M. Macphee, M. J. Day and D. W. Mason, Immunology 70, 527–534 (1990). Other illustrative autoantigens susceptible to use in this invention comprise heat shock proteins, the 64 Kd protein of $\beta$ cells of the pancreas and human myelin basic protein.

The antigen can be conjugated in any convenient manner which does not denature the anti-IgD antibody or interferes with the binding sites. This will include most of the conventional ways of covalently bonding two proteins, e.g. in enzyme-labelled antibody or hapten-carrier technology. Use of a single divalent molecule which can react with groups on the antigen and the anti-IgD is preferred. An "immunological" conjugate in which the antigen (1) is linked to the antibody (2) by a divalent (bispecific) antibody is an alternative possibility.

Conveniently, a cysteine residue is added to the autoantigen of interest, in order to provide a functional sulphydryl group, which can then react with a melaiimide type of linker, especially sulfo-SMCC, N-sulfosuccinyl-4-[(N-maleiimido)methyl]cyclohexylcarbamate.

The antibody can be of any kind, but is preferably monoclonal. A monoclonal antibody can be made by screening hybridomas made by the conventional method from a mouse myeloma and the spleen cells of mice in which antibodies to human cell surface antigens have been raised. The hybridomas can be screened on B cells; those which secrete antibodies whose binding to B cells is inhibited by IgD myeloma protein are selected. IgD myeloma proteins are preparable as described by F. D. Finkelman et al., J. Immunol. 126, 680 (1981). One such antibody is MRC-OX-60 which is available from the present inventor, Dr. D. W. Mason at the MRC Cellular Immunology Unit, Sir William Dunn School of Pathology, South Parks Road, Oxford OX1 3RE, England. Another such antibody is MARD-3 produced by Dr. H. Bazin, at the University of Louvain, Belgium. However, it is also possible to use a polyclonal antibody which has an isotype monospecificity to IgD, as was used by F. D. Finkelman et al., J. Immunology 137, 2878–2885 (1986).

The antibodies can be used as in the form of an antigen-binding fragment such as Fab or F(ab')$_2$ dimer. Single domain antibodies from isolated hypervariable domains can also be used. The fragments can be humanised so that the binding region is that of the mouse monoclonal antibody and the remainder is of human antibody.

In addition to the control of autoimmune responses the principle of the invention clearly indicates that any disease caused by an invasive antigen which invokes a harmful cell-mediated immune response is likely to be treatable by use of the invented conjugates.

In order to explain why the invention is of more general applicability than merely to conjugates of anti-IgD with autoantigens, reference is made to FIG. 1 which is a greatly simplified and purely schematic representation of the relevant cells of the immune system and the effects of the various lymphokines produced. The left-hand side (LHS) of FIG. 1 represents the desired type of immune response wherein B cells produce a humoral response and are aided in doing so by a sub-population of T helper cells designated type 2 (Th$_2$). The right-hand side (RHS) represents an undesired type of immune response of the "cell-mediated" type, whereby macrophages kill pathogens by phagocytosis and are aided in doing so by a sub-population of T helper cells designed type 1 (Th$_1$). Although the precise mechanism by which the cell-mediated response to autoantigens produces harmful symptoms, e.g. inflammation of the joints in rheumatoid arthritis, is not understood, it is known that suppression of the cell-mediated response is associated with alleviation of the symptoms. Consequently, it is an objective to enhance the humoral response (LHS) and suppress the cell-mediated response (RHS). B-cells and Th$_2$ cells have a positive feedback mechanism, by which B cells present antigen, in the form of a MHC II-antigen complex, to T cells. When the T cells see the complex they are induced to differentiate into specialised Th$_2$ cells, producing IL-4 and IL-10. The IL-4 feeds back to the B cells, stimulating the expression of Class II MHC on their surface, which in turn enables more antigen to be presented to the T helper cells. These stimulatory processes, shown by solid lines, are accompanied by inhibitory processes, shown by broken lines, acting on the cells which take part in the cell-mediated response. Thus IL-10, apparently produced by B cells and Th$_2$ cells, reduces the ability of macrophages to secrete TNF-$\alpha$ and PGE-2 and also inhibits lymphokine production, notably of gamma-interferon (IFN-$\gamma$), by Th$_1$ cells. TNF-$\alpha$, PGE-2 and IFN-$\gamma$ are all mediators of inflammation. The IL-4, produced by the Th$_2$ cells also reduces TNF-$\alpha$ and PGE-2 secretion by macrophages and, by a poorly understood mechanism, inhibits the growth of Th$_1$ type cells.

In the present invention a way has been found of tipping the balance of the immune system away from cell-mediated to humoral response. The invention makes use of a B cell surface antigen, such as IgD (which can be regarded as an antigen in the context) to bind a ligand such as anti-IgD to it and via the anti-IgD, a further ligand, viz. the antigen (1) of interest such as an autoantigen. This antigen is then re-presented on the surface of the B cell as a Class II-MHC complex. The immune system then becomes "primed" to create further Th$_2$ cells (specific to the autoantigen) when the B cells later encounter that autoantigen.

From these considerations it will be seen that the invention is likely to work with B cells having any non-interfering surface molecule to which the antigen of interest can be bound via an antibody. However, the immunogen must not be one which occurs elsewhere in the body to a greater extent than on B cells. Thus, of the immunoglobulins found on B cells, only IgD is a serious contender, because it alone is found in serum only in very low concentrations. It is possible to use antibodies to MHC II. In principle it can be expected that the antibody could be raised against any genetic region of MHC II, but we have so far obtained better results from an anti-MHC II (I-E) antibody than from an anti-MHC (I-A), although the latter does show some effect. Other surface antigens might yet be discovered.

It will also be apparent that the invention is not restricted to autoantigens; any infection which gives rise to a cell-mediated component by the immune system is treatable by the invention. As yet, the antigens responsible are not clearly identified and characterised, but the infections in which they occur, e.g. tuberculosis and leprosy, are well known and it is only a matter of time before the specific antigens implicated in the cell-mediated action are identified.

The conjugates are administered to patients in small amounts, preferably without any carrier or adjuvant. They will normally be administered by intravenous injection, in amounts of 0.1 to 1 mg./kg. bodyweight.

The following Example illustrates the invention. "SEPHADEX" is a Registered Trade Mark (SEPHADEX is a beaded gel prepared by cross-linking dextran with epichlorohydrin under alkaline conditions).

EXAMPLE 1

A conjugate was prepared form guinea-pig myelin basic protein, peptide residues 70-86 (see above; the sequence is given in I. A. M. Macphee et al, cited above) and the anti-IgD monoclonal antibody MRC-OX-60 (see above). The MBP peptide was coupled through a cysteine residue introduced at its N-terminal end in order to provide a ready means of conjugating it with a maleiimide type cross-linking agent. Conjugation was done in two stages. First the crosslinker was coupled to the anti-IgD antibody using 8 mg sulpho-SMCC in 0.5 ml phosphate buffered saline (PBS) and 8 mg MRC-OX-60 IgG (or F(ab')$_2$ prepared by pepsin digestion) also in 0.5 ml PBS. Unreacted crosslinker was removed by gel filtration on a "SEPHADEX" G-25 column. Second, the MBP peptide (0.7 mg/1 mg OX60-IgG) was reacted with the OX-60 cross-linker complex at pH6.0. Separation between conjugate and unconjugated peptide was achieved by gel filtration on a "SEPHADEX" G-50 column. Efficiency of conjugation was checked by amino acid analysis. The conjugate (varying amounts from 25 to 100 μg) and, for comparison, unconjugated MBP peptide (20

μg) and MBP peptide conjugated to BSA (100 μg) were injected intravenously into rats which were then immunised subcutaneously with MBP (100 μg) in Freud's Complete Adjuvant. Control rats were given the MBP/FCA immunisation. A boosting, second i.v. injection of the conjugate was given 7 days later and the control rats were given a second dose of their first treatment.

Figure 2:
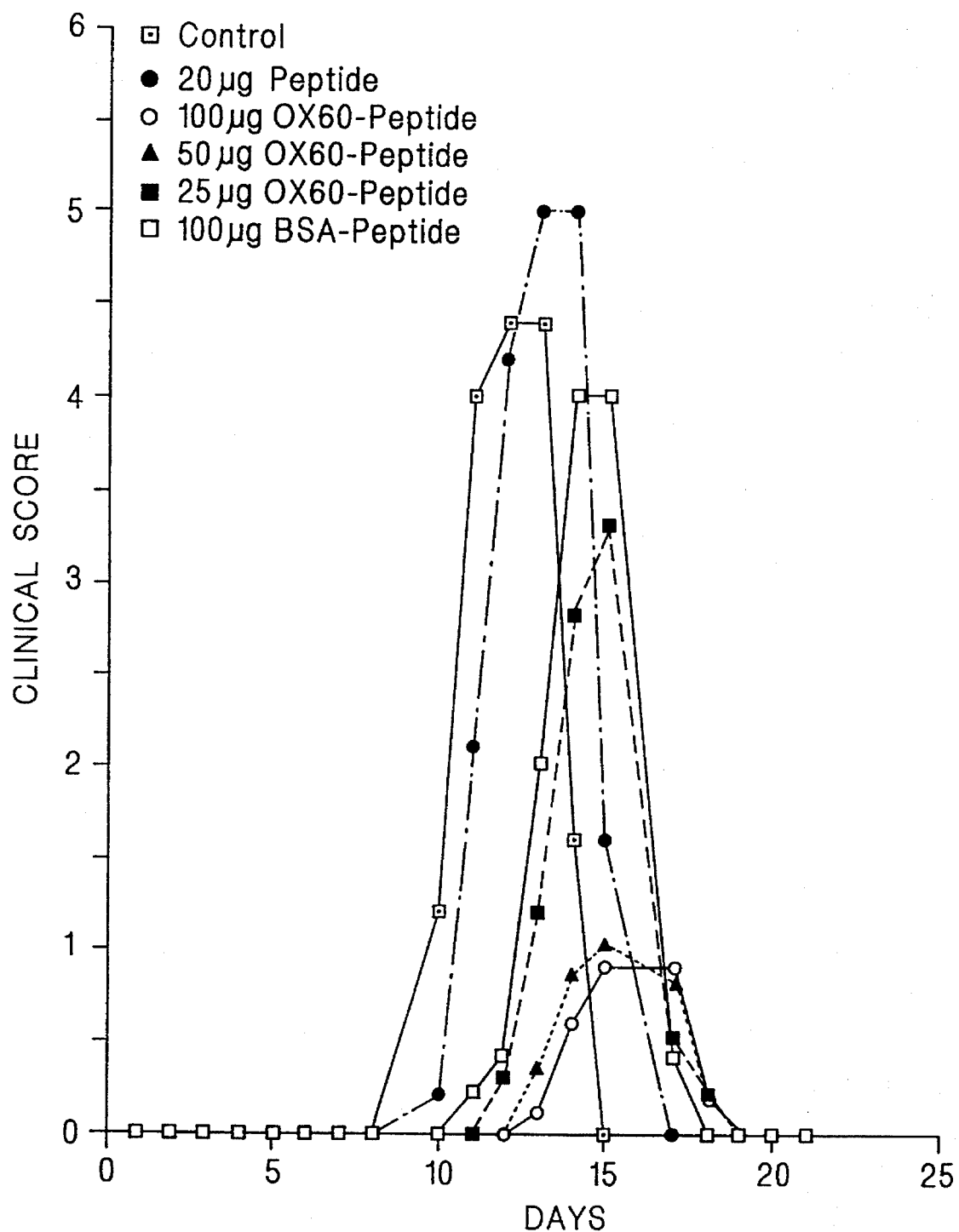

The results are shown graphically in FIG. 2 in which the clinical severity of the EAE disease, as estimated by a standard scoring procedure, is plotted on the ordinate and the time course of the experiment in days is plotted on the abscissa. Injections with the MBP alone or with the BSA-MBP conjugate gave no significant protection compared with the control. However, 25 μg of the peptide-antibody complex (filled square) had some suppressing effect, while remarkably good suppression was achieved at the two higher doses of peptide (open circle and square filled except for a central dot). At the higher doses some rats developed no disease at all.

EXAMPLE 2

The myelin basic protein peptide of Example 1 was used in this Example, alone or conjugated to the monoclonal anti-IgD antibody MRC-OX-60, an F(ab')$_2$ fragment thereof, the monoclonal anti-(human complement) antibody MRC-OX-21 or the monoclonal anti-(rat MHC II genetic region I-E) antibody MRC-OX-17. In all cases the antibody was in the form of IgG. The conjugate contained approximately 10 peptide groups/IgG molecule or fragment thereof.

All rats were immunized in the hind footpads with 50 μg guinea-pig myelin basic protein in Freunds' complete adjuvant (FCA) on day 0 of the experiments. In some cases control rats received injections of phosphate buffered saline (PBS) intravenously on the day of immunization and again 7 days later while others received no PBS injections. All other groups received the stated doses of peptide conjugates intravenously on day 0 and day 7 and there were 5 rats in each of these groups. Each experiment had a control group immunized with the same MBP/FCA preparation but, as the severity of disease was similar in each case, the data were pooled (23 rats).

Paralysis was scored on a Scale of 1–5 as follows:

1-limp tail, 2 hindlimb weakness, 3-unilateral hindlimb paralysis, 4-bilateral hindlimb paralysis, 5-bilateral hindlimb paralysis+urinary incontinence (female) or urinary retention (male).

The groups and their average severity scores were as follows:

| Group 1 | Controls | 4.3 |
| Group 2 | 100 μg bovine serum albumin-peptide conjugate | 4.3 |
| Group 3 | 20 μg unconjugated peptide | 5.0 |
| Group 4 | 100 μg anti-IgD MAb | 4.4 |
| Group 5 | 100 μg MRC-OX-21-peptide conjugate (MRC-OX-21 is a MAb against a human complement component. It has the same IgG$_1$ isotype as MRC-OX-60, the anti-IgD MAb | 4.2 |
| Group 6 | anti-IgD F(ab')$_2$-peptide conjugate | 0.9 |
| Group 7 | 50 μg anti-IgD-peptide conjugate | 0.8 |
| Group 8 | 100 μg anti-IgD-peptide conjugate | 0.2 |
| Group 9 | 100 μg MRC-OX-17 peptide conjugate (MRC-OX-17 is a MAb against MHC II genetic region I-E) | 0.4 |

Groups 6–9 (according to the invention) showed highly significant reductions in disease severity compared to controls ($p<0.001$ in all cases by Wilcoxon Rank—Sum test). It is particularly noteworthy that the anti-MHC II antibody conjugate of group 9 gave a result similar to that of the anti-IgD conjugate, thus confirming the wide applicability of the invention.

I claim:

1. A conjugate consisting essentially of (1) an autoantigen which is a peptide which when present in the body gives rise to a harmful cell-mediated immune response with (2) an antibody to IgD surface molecules present predominantly on B cells.

2. A conjugate according to claim 1, wherein the antibody (2) is a monoclonal antibody.

3. A method of treating a patient suffering from a disease associated with the cell-mediated immune response, said method comprising the step of administering to the patient a disease-alleviating amount of a conjugate consisting essentially of (1) an autoantigen which is a peptide which when present in the body gives rise to a harmful cell-mediated response with (2) an antibody to IgD surface molecules present predominantly on B cells.

4. A method according to claim 3, wherein antibody (2) is a monoclonal antibody.

* * * * *